US009804067B2

(12) United States Patent
Adachi et al.

(10) Patent No.: US 9,804,067 B2
(45) Date of Patent: Oct. 31, 2017

(54) OBSERVATION AND PHOTOGRAPHY APPARATUS

(71) Applicants: Kagoshima University, National University Corporation, Kagoshima-shi, Kagoshima (JP); Nakayamadenki Co., Ltd., Shijonawate-shi, Osaka (JP)

(72) Inventors: Yoshitaka Adachi, Kagoshima (JP); Makoto Nakayama, Shijonawate (JP)

(73) Assignees: KAGOSHIMA UNIVERSITY, NATIONAL UNIVERSITY CORPORATION, Kagoshima (JP); NAKAYAMADENKI CO., LTD., Osaka (JP)

(*) Notice: Subject to any disclaimer, the term of this patent is extended or adjusted under 35 U.S.C. 154(b) by 400 days.

(21) Appl. No.: 14/408,762

(22) PCT Filed: Jun. 18, 2013

(86) PCT No.: PCT/JP2013/066684
§ 371 (c)(1),
(2) Date: Dec. 17, 2014

(87) PCT Pub. No.: WO2013/191165
PCT Pub. Date: Dec. 27, 2013

(65) Prior Publication Data
US 2015/0185123 A1    Jul. 2, 2015

(30) Foreign Application Priority Data
Jun. 21, 2012 (JP) .................. 2012-140047

(51) Int. Cl.
*G01N 1/32* (2006.01)
*H01L 21/321* (2006.01)
(Continued)

(52) U.S. Cl.
CPC .............. *G01N 1/32* (2013.01); *B23H 5/06* (2013.01); *B23H 5/08* (2013.01); *B24B 37/046* (2013.01);
(Continued)

(58) Field of Classification Search
CPC ..... H01L 21/32125; C25F 7/00; B24B 37/046
See application file for complete search history.

(56) References Cited

U.S. PATENT DOCUMENTS

2002/0081015 A1    6/2002  Alkemper et al.
2004/0067718 A1*   4/2004  Shimizu .................. B23H 5/08
                                                      451/6
2011/0217905 A1    9/2011  Akiyama et al.

FOREIGN PATENT DOCUMENTS

CN    101265580    9/2008
CN    101383281    3/2009
(Continued)

OTHER PUBLICATIONS

Chinese Office Action dated May 5, 2016.
European Search Report dated May 12, 2016.

*Primary Examiner* — Nicholas A Smith
(74) *Attorney, Agent, or Firm* — Rankin, Hill & Clark LLP

(57) ABSTRACT

An observation and photography apparatus that has a polishing mechanism attached thereto. The polishing mechanism is provided with a turntable with a perpendicular rotation shaft, a polishing cloth for polishing the surface of a sample attached to the bottom surface of the turntable, and a polishing-fluid spraying nozzle disposed below the polishing cloth for spraying polishing fluid containing polishing material upward to we the polishing cloth.

6 Claims, 11 Drawing Sheets

(51) Int. Cl.
*C25F 7/00* (2006.01)
*B23H 5/08* (2006.01)
*B24B 37/04* (2012.01)
*C25F 3/16* (2006.01)
*B23H 5/06* (2006.01)
*B24B 37/10* (2012.01)
*C25F 3/00* (2006.01)
*B24B 37/24* (2012.01)
*B24B 37/26* (2012.01)
*B24B 49/12* (2006.01)
*B24B 57/02* (2006.01)
*G02B 21/26* (2006.01)
*G02B 21/36* (2006.01)
*B24B 37/34* (2012.01)

(52) U.S. Cl.
CPC .............. *B24B 37/10* (2013.01); *B24B 37/24* (2013.01); *B24B 37/26* (2013.01); *B24B 37/345* (2013.01); *B24B 49/12* (2013.01); *B24B 57/02* (2013.01); *C25F 3/00* (2013.01); *C25F 3/16* (2013.01); *C25F 7/00* (2013.01); *G02B 21/26* (2013.01); *G02B 21/367* (2013.01); *H01L 21/32125* (2013.01)

(56) References Cited

FOREIGN PATENT DOCUMENTS

| EP | 1 103 346 | 5/2001 |
|----|-----------|--------|
| JP | 07-325041 | 12/1995 |
| JP | 11-151663 | 6/1999 |
| JP | 2004-142086 | 5/2004 |
| JP | 2005-103696 | 4/2005 |

\* cited by examiner

FIG. 7
(a) 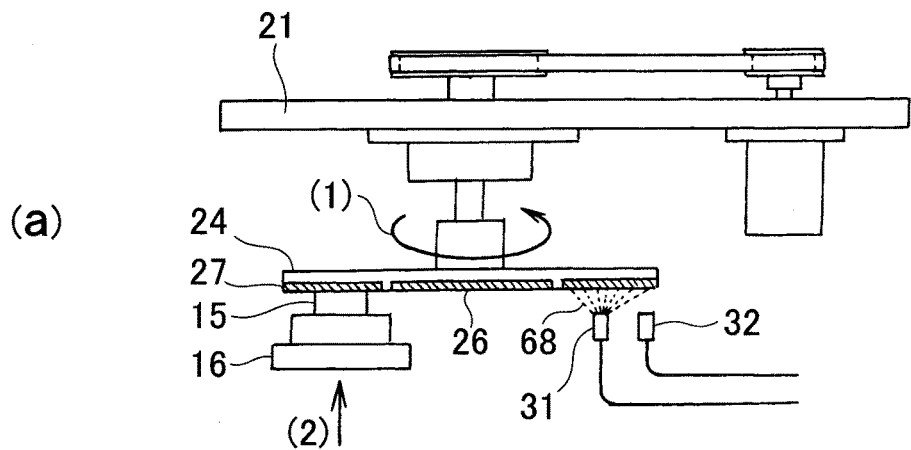
(b) 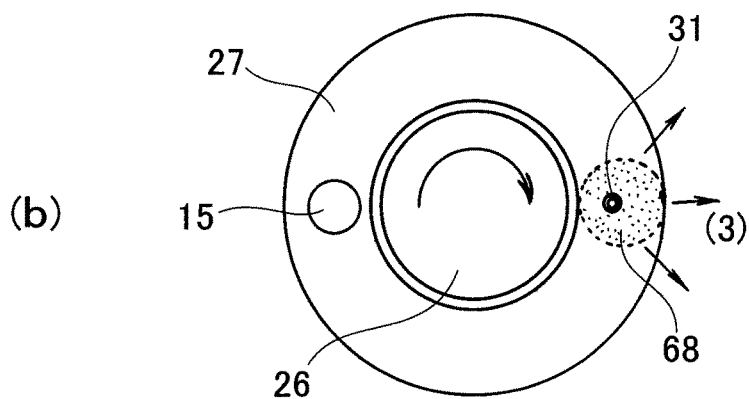
(c) 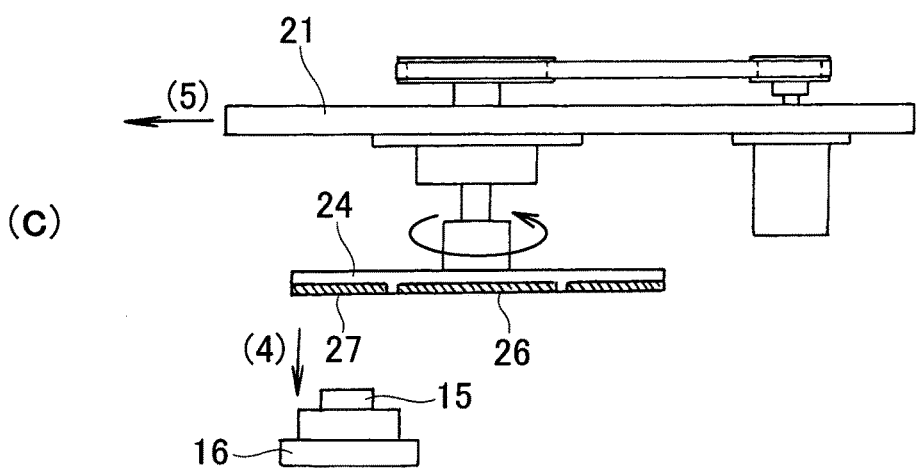

FIG.8
(a) 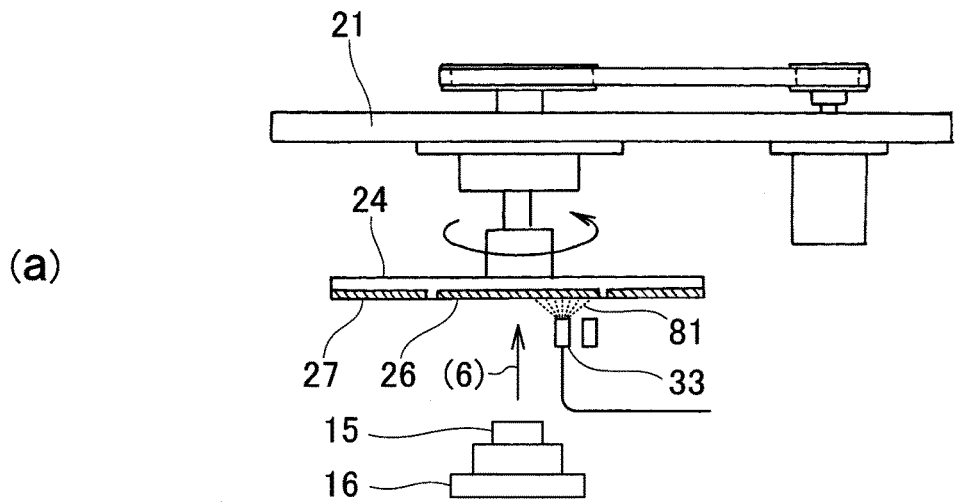
(b) 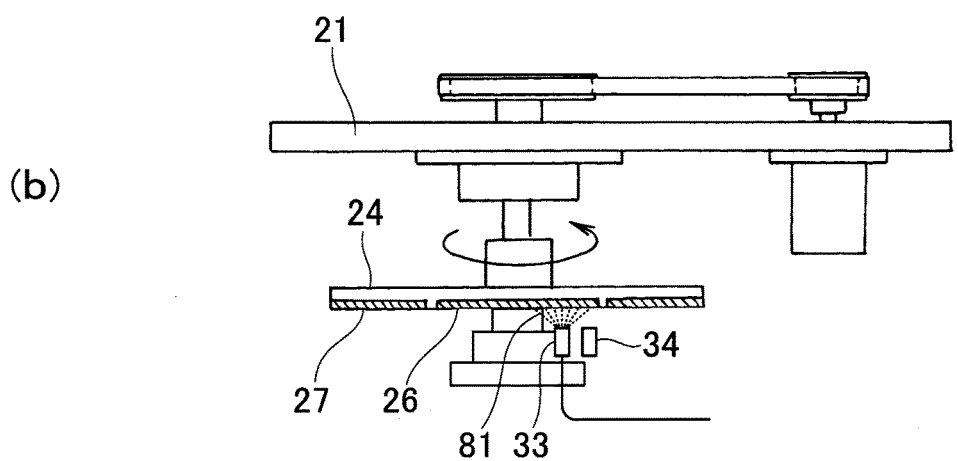
(c) 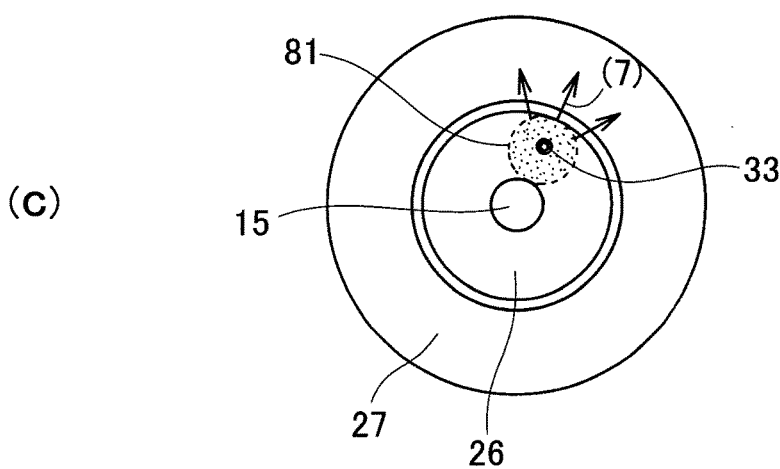

FIG.10
(a)
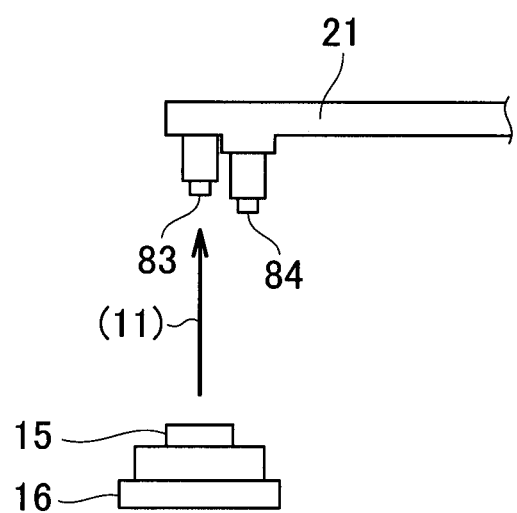
(b)
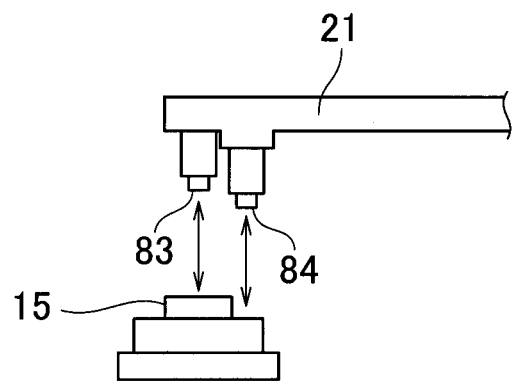

OBSERVATION AND PHOTOGRAPHY APPARATUS

TECHNICAL FIELD

The present invention relates to an observation and photography device in which a polishing mechanism for polishing a sample is attached to a photography unit-equipped microscope for magnifying and photographing a sample.

The photography unit-equipped microscope observes and photographs the surface of a sample.

The polishing mechanism repeatedly physically and chemically polishes the surface of a sample at equidistance intervals or for a set amount.

The sample is etched, as required, which is advantageous for observation.

An image obtained by the observation device undergoes 3D construction and is used for 3D observation and/or quantification of the sample.

The observation and photography device corresponds to a device for automatically carrying out observation referred to as serial sectioning.

BACKGROUND ART

Various observation and photography devices for photographing and observing the surface of a sample are known (e.g., see Patent Literature 1).

Patent Literature 1 will be described with reference to FIG. 12 hereof.

FIG. 12 illustrates the basic principle of a conventional observation and photography device. The surface of a sample 101 is observed using a microscope 102, as shown in FIG. 12. The surface of the sample 101 is photographed using a photography unit 103 attached to the microscope 102 and is recorded in the form of an image.

When the sample 101 is a metal material, the surface of the sample 101 is mirror-finished by a polishing mechanism prior to observation and/or photography.

Various polishing mechanisms for polishing the sample 101 have been proposed (e.g., Patent Literature 2).

Patent Literature 2 will be described with reference to FIG. 13 hereof.

FIG. 13 illustrates the basic principle of a conventional polishing mechanism. The sample 101 is placed on a rotating table 105, as shown in FIG. 13. A polishing liquid 106 containing very small polishing particles is fed from a down-facing nozzle 108 to the sample 101. A polishing liquid 106 containing polishing particles flows over the upper surface of the sample 101 by centrifugal force. The upper surface of the sample 101 is polished by bringing a rotating polishing cloth 107 into contact with the upper surface of the sample 101. Observation is carried out using the microscope 102 indicated by an imaginary line and photography is carried out using the photography unit 103.

A portion of the very small polishing particles bites into the polishing cloth 107 and stays on the polishing cloth 107. The polishing particles are crushed upon use. The broken surfaces are sharp and damage the sample 101 when not removed. Crushed polishing particles are left behind on the upper surface of the sample 101 as well. A portion of the shaved sample damages the sample 101, which roughens the upper surface of the sample 101 and reduces the quality of the sample 101.

Washing or replacing the polishing cloth 107 can prevent a reduction in quality. When the polishing cloth is to be replaced, the polishing mechanism must be stopped; therefor, the operation life of the observation and photography device is reduced.

Moreover, the crushed polishing particles bite into the polishing cloth 107. When the polishing cloth is washed, the polishing particles are scraped off from the polishing cloth 107 using a spatula or a squeegee. The polishing cloth 107 gets damaged by the spatula or squeegee, and time is required to wash away the polishing particles using a large amount of washing liquid.

When washing is carried out, the service life of the polishing cloth 107 is reduced and large amounts of washing liquid are required.

In terms of smoothly and efficiently performing experiments, it is not advantageous for the service life of the polishing cloth to be reduced and for the required amount of washing liquid to be increased. Therefore, there is a need for an observation and photography device allowing the required amount of washing liquid to be reduced.

Polishing has been conventionally carried using electrolysis. The surface of the sample can be smoothed by electrolytic polishing. An electrolytic polishing sheet and electrolytic polishing cloth or electrolytic bath are generally required to perform electrolysis. Therefore, the electrolytic polishing sheet and electrolytic polishing cloth or electrolytic bath must be separately provided, increasing the size of the polishing mechanism. There is a need to reduce the size of the polishing mechanism.

In electrolysis, the surface of the sample becomes fouled by the solute components of the sample. It is possible to prevent polluting by replacing the electrolyte after each use. However, large volumes of electrolyte are required. There is a need to reduce the required amount of electrolyte.

The amount of polishing must be measured in a polishing mechanism. The amount of polishing is very low; i.e., 100 nm to several tens of microns. A measurement device for measuring the amount of polishing is supported on the machine stand via a support, and when the support deforms, errors occur in the measurement value relating to the amount of polishing. Also, when the sample stand (rotating table, or the like) on which the sample is placed deforms, errors occur in the measurement value relating to the amount of polishing.

In a conventional structure, it is difficult to increase the precision for measuring the amount polishing. Consequently, there is a need for a structure capable of increasing the precision for measuring the amount of polishing.

The surface of the sample may be corroded by chemicals prior to observation of the sample surface. This method is referred to as chemical etching.

When the corrosive liquid splashes and makes contact with the microscope and/or the device for measuring the amount of polishing, the microscope and/or the device for measuring the amount of polishing can be damaged, which is a problem that needs to be addressed.

In FIG. 13, the microscope 102 is adjusted so that a focal point is established on the upper surface of the sample 101. Because adjusting the microscope 102 is laborious, the focal point is adjusted prior to observation.

However, the surface is lowered when the sample 101 is repeatedly polished with the polishing cloth 107. The focal point falls out of alignment when the surface is lowered, and the image becomes blurred. There is a need to obtain a sharp image even when the surface is lowered.

Photographs are taken while the microscope 102 is moved along the surface of the sample 101, polishing is carried out, and photographs are taken while the microscope 102 is repeatedly moved along the surface of the sample 101. The acquired images can be layered to produce a stereoscopic image.

The microscope 102 may not accurately return to its original position due to mechanical error such as backlash. The image becomes less clear when such error occurs.

There is a need to obtain a clear image even when the microscope 102 moves.

PRIOR ART LITERATURE

Patent Literature 1: JP H07-325041 A
Patent Literature 2: JP H11-151663 A

SUMMARY OF INVENTION

Technical Problem

An object of the present invention is to provide an observation and photography device provided with a physical and chemical polishing mechanism, wherein the required amount of washing liquid can be reduced, good precision for measuring the polishing amount and a good observation image can be obtained while ensuring the device is kept compact overall, performance in terms of maintenance and durability are excellent, and a clear image can be obtained even when the microscope moves.

Solution to Problem

According to one aspect of the present invention, there is provided an observation and photography device in which a polishing mechanism is attached to a photography unit-equipped microscope capable of observing and photographing the surface of a sample, the polishing mechanism repeatedly polishing a surface of the sample in equidistant intervals or by an established amount in the vertical direction prior to observation, characterized in that the polishing mechanism comprises: a turntable with a vertical rotation shaft; a polishing cloth for polishing the surface of the sample, the polishing cloth being attached to the lower surface of the turntable; and a polishing-liquid spray nozzle for spraying a polishing-material-containing polishing liquid upward to wet the polishing cloth, the polishing-liquid spray nozzle being disposed below the polishing cloth.

Desirably, the polishing cloth comprises an inner polishing cloth disposed centrally on the lower surface of the turntable, and at least one outer polishing cloth disposed on the lower surface of the turntable so as to surround the inner polishing cloth.

It is desirable that the inner polishing cloth have a finer mesh than the outer polishing cloth.

According to another aspect of the present invention, there is provided an observation and photography device in which an electrolytic polishing mechanism is attached to a photography unit-equipped microscope capable of observing and photographing the surface of a sample, the electrolytic polishing mechanism repeatedly electrolytically polishing a surface of the sample in equidistant intervals or by an established amount in the vertical direction prior to observation, characterized in that the electrolytic polishing mechanism comprises: a turntable having a vertical rotation shaft; an electrolyte-absorbing cloth for absorbing an electrolyte for electrolytically polishing the observation plane, the electrolyte-absorbing cloth being attached to the lower surface of the turntable; and an electrolyte-spraying nozzle for spraying the electrolyte upward to wet the electrolyte-absorbing cloth, the electrolyte-spraying nozzle being disposed below the electrolyte-absorbing cloth.

Desirably, corrosive liquid is sprayed from the electrolyte-spraying nozzle.

It is preferred that the observation and photography device further comprise a gauge for gauging the distance to the surface of the sample or to the observation plane, and a calculation unit for calculating the amount of polishing from the difference between the distance prior to polishing and the distance after polishing as gauged by the gauge.

In a preferred form, the observation and photography device further comprises a gauge for gauging the distance to the surface of the sample or to the observation plane, and a statistical processing unit for measuring a plurality of locations on the surface or in the observation plane using the gauge, and statistically processing the plurality of resulting values to determine surface roughness.

It is desired that the turntable be disposed inside a cylindrical cover, the photography unit-equipped microscope be disposed outside the cylindrical cover, and the spray area of the polishing-liquid spray nozzle or the electrolyte spray nozzle be set inside the cylindrical cover.

Preferably, the device further comprises a sample stand-elevating mechanism for moving the electrolytically or non-electrolytically polished sample to an observation position of the photography unit-equipped microscope, and a control unit for estimating the amount of polishing and controlling the sample stand-elevating mechanism so that the surface or the observation plane aligns with the focal point of the photography unit-equipped microscope.

It preferred that the photography unit-equipped microscope be attached to a stage that moves horizontally, and the control unit save an image prior to movement by the stage and has a control function for controlling the stage so that the photography unit-equipped microscope which has been moved by the stage returns to the original position on the basis of the image prior to movement.

Advantageous Effects of Invention

In accordance with the one aspect of the present invention, the polishing liquid spray nozzle is disposed below the polishing cloth, and the polishing liquid is sprayed upward from the polishing liquid spray nozzle.

The polishing liquid falls strikes the lower surface of the polishing cloth, wets the polishing cloth, and is provided to wet polishing. The polishing liquid falls from the polishing cloth due to gravity. Polishing material (particles) provided to the polishing and then crushed drop together with the polishing liquid. Specifically, degraded polishing liquid is rapidly separated from the polishing cloth.

Since degraded polishing liquid is not retained on the polishing surface, there is no concern of unnecessary damage to the polishing surface, and the quality of the sample can kept high. Since degraded polishing liquid is not retained on the polishing surface, there is no need to wash using large volumes of washing liquid, allowing the required amount of washing liquid to be reduced.

Consequently, in accordance with the present invention, there is provided the observation and photography device provided with the polishing mechanism, wherein the required amount of washing liquid can be reduced.

According to the invention, the inner polishing cloth and the outer polishing cloth are disposed centrally on the lower surface of the turntable.

Varying the roughness of the inner polishing cloth and the outer polishing cloth makes it possible to perform rough polishing and finishing. Even when the inner polishing cloth and outer polishing cloth have the same roughness, varying the particle diameter of the polishing material contained in the polishing liquid to be supplied makes it possible to perform rough polishing and finishing. As a result, rough polishing and finishing can be performed using a single turntable on which an inner polishing cloth and an outer polishing cloth are disposed.

The present invention can provide a more compact observation and photography device than when a turntable for rough polishing and a turntable for finishing polishing are provided.

According to the invention, the inner polishing cloth has a finer mesh than the outer polishing cloth.

Rough polishing is performed using the outer polishing cloth and finishing is performed using the inner polishing cloth near the center of rotation.

A polishing material having a relatively large particle diameter is used in rough polishing. It is undesirable for a large-particle-diameter polishing material to be deposited on the inner polishing cloth. When a polishing liquid containing a large-particle-diameter polishing material is sprayed onto the outer polishing cloth, the polishing liquid is flung radially outward due to centrifugal force, which eliminates any concern that the polishing liquid will infiltrate the inner polishing cloth.

Polishing liquid containing small-particle-diameter polishing material is sprayed toward the inner polishing cloth. The polishing liquid is flung radially outward due to centrifugal force and infiltrates the outer polishing cloth, but since the particle diameter of the polishing material is small, rough polishing remains unaffected.

In accordance with another aspect of the invention, an electrolyte-absorbing cloth and an electrode are provided to the turntable. The observation and photography device can be made more compact than when an electrolytic polishing sheet or an electrolytic polishing bath are separately provided.

Excess electrolyte drops from the electrolyte-absorbing cloth due to gravity. When electrolyte is supplied during electrolysis, fouled electrolyte drops together with the electrolyte. Specifically, degraded electrolyte rapidly separates from the electrolyte-absorbing cloth.

Since degraded electrolyte is not retained on the surface of the electrolyte-absorbing cloth, there is no concern that superfluous foulants will be deposited on electrolyzing surface, and the quality of the sample can kept high. Since the degraded electrolyte is not retained on the processing surface, there is no need to wash using large volumes of washing liquid, and the required amount of electrolyte can be reduced.

The present invention can provide a more compact observation and photography device than when a turntable for rough polishing, a turntable for finishing, and an electrolytic polishing sheet or electrolytic bath are all provided.

In the invention, a corrosive liquid is sprayed from the electrolyte-spraying nozzle. This enables the sample to be etched, and applications of the observation and photography device to be enlarged in scope.

In the invention, the observation and photography device further comprises: the distance gauge, and the calculation unit for calculating the amount of polishing from the difference between the distance prior to polishing and the distance after polishing. The amount of polishing can be accurately determined in a simple manner.

In the invention, the observation and photography device may further comprise: the distance gauge provided with a statistical processing unit for measuring a plurality of locations on the surface or in the observation plane using the gauge and statistically processing the plurality of resulting values to determine surface roughness; and the calculation unit for calculating the amount of polishing from the difference between the distance prior to polishing and the distance after polishing as gauged.

Surface roughness can be determined in parallel to observation of the sample, and applications for the observation and photography device are enlarged in scope.

In the invention, the turntable is disposed inside a cylindrical cover while the photography unit-equipped microscope is disposed outside the cylindrical cover. The spray area of the polishing-liquid spray nozzle or the electrolyte spray nozzle may set inside the cylindrical cover. The polishing liquid or electrolyte sprayed from the nozzle is retained inside the cylindrical cover. There is no concern that liquid droplets will land on the microscope disposed outside the cylindrical cover.

According to the present invention, the observation and photography device may further comprise a control unit for estimating the amount of polishing and controlling the sample stand-elevating mechanism so that the surface or the observation plane aligns with the focal point of the photography unit-equipped microscope. A good image can be constantly obtained by the operation of the control unit.

In accordance with the invention, the control unit saves an image prior to movement by the stage and has a control function for controlling the stage so that the photography unit-equipped microscope which has been moved by the stage returns to the original position on the basis of the image prior to movement. Backlash and other mechanical errors are inevitably included in the stage, and, when ignored, reduce the clarity of the image. In accordance with the present invention, the control unit accurately returns the microscope to its original position, even when there is backlash or other mechanical error.

BRIEF DESCRIPTION OF DRAWINGS

FIG. 7 is an operational view of a polishing mechanism by an outer polishing cloth;

FIG. 8 is an operational view of the polishing mechanism by an inner polishing cloth;

FIG. 10 is an operational view of a laser measurement device;

DESCRIPTION OF EMBODIMENTS

Embodiments of the present invention will be described in detail below with reference to the accompanying drawings.

Embodiments

Figure 1:
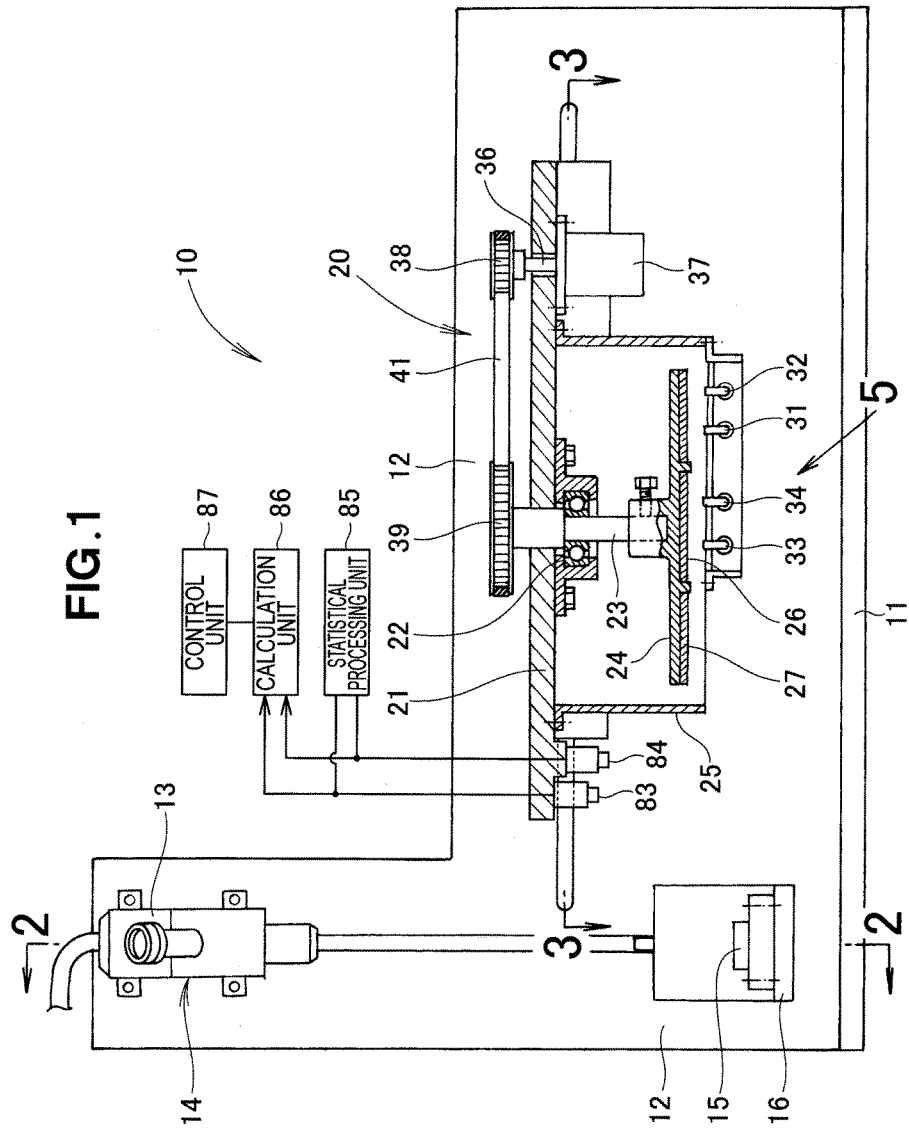
FIG. 1 is a front view of the observation and photography device according to the present invention.

As shown in FIG. 1, an observation and photography device 10 comprises a horizontally extending base plate 11, a wall plate 12 standing upright from the base plate 11, a microscope 14 secured to the upper part of the wall plate 12 and provided with a photography unit 13, a sample stand 16 for supporting a sample 15 and elevatably provided to the wall plate 12 below the microscope 14, and a polishing mechanism 20 provided to the wall plate 12 so as to be capable of horizontal movement.

The polishing mechanism 20 comprises: a slider 21 that moves horizontally; a rotation shaft 23 vertically attached to the slider 21 interposed by a bearing 22; a turntable 24 attached to the lower end of the rotation shaft 23; a cylindrical cover 25 suspended from the slider 21 so as to surround the turntable 24; an inner polishing cloth 26 and an outer polishing cloth 27 provided to the lower surface of the turntable 24; a first polishing-liquid spray nozzle 31 for spraying polishing liquid upward toward the outer polishing cloth 27, the first polishing-liquid spray nozzle being secured to the lower end of the cylindrical cover 25 and disposed below the outer polishing cloth 27; a first washing-liquid spray nozzle 32 for spraying washing liquid upward toward the outer polishing cloth 27, the first washing-liquid spray nozzle being secured to the lower end of the cylindrical cover 25 and disposed below the outer polishing cloth 27; a second polishing-liquid spray nozzle 33 for spraying polishing liquid upward toward the inner polishing cloth 26, the second polishing-liquid spray nozzle being secured to the lower end of the cylindrical cover 25 and disposed below the inner polishing cloth 26; a second washing-liquid spray nozzle 34 for spraying washing liquid upward toward the inner polishing cloth 26, the second washing-liquid spray nozzle being secured to the lower end of the cylindrical cover 25 and disposed below the inner polishing cloth 26; a turntable drive motor 37 attached to the slider 21 so that a motor shaft 36 is parallel to the rotation shaft 23; a drive pulley 38 attached to the motor shaft 36; a driven pulley 39 secured to the upper end of the rotation shaft 23; and a belt 41 mounted around the drive pulley 38 and the driven pulley 39.

The turntable 24 is turned at a predetermined speed in a predetermined direction by the turntable drive motor 37. The belt 41 is preferably a timing belt (a toothed belt), but may be a chain. When a chain is used, the pulleys 38, 39 are replaced by a sprocket.

Preferably, non-contact-type laser measurement devices 83, 84 are attached side-by-side to one end of the slider 21 nearest to the sample stand 16. The laser measurement devices 83, 84 are disposed above the nozzles 31 to 34. The laser measurement devices 83, 84 are furthermore disposed outside the cylindrical cover 25.

Figure 2:
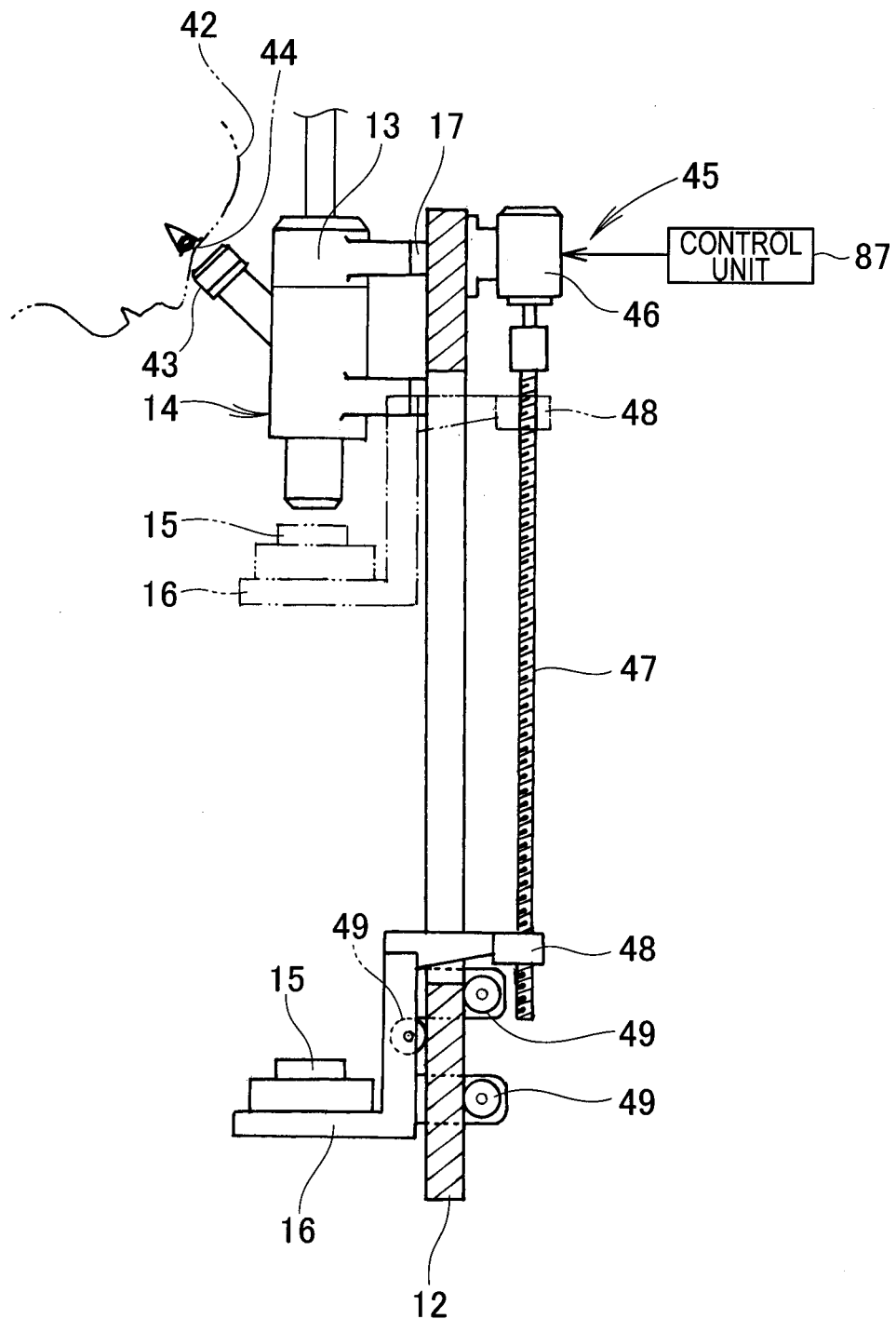
FIG. 2 is a cross-sectional view taken along line 2-2 of FIG. 1.

The microscope 14 is attached to the wall plate 12 via a manual or motor-driven XY stage 17 that moves in the horizontal direction, as shown in FIG. 2.

An observer 42 brings his/her eye 44 close to the eyepiece 43, whereby the upper surface of the sample 15 indicated by an imaginary line can be viewed. The upper surface of the sample 15 can be photographed using the photography unit 13 provided to the microscope 14.

The microscope 14 is capable of moving horizontally about 1 cm by the operation of the stage 17. The observer 42 can carry out observation without changing posture.

Since the microscope 14 is attached to the wall plate 12, the height from the floor does not change. The observer 42 can carry out observations in a fixed posture.

A sample stand-elevating mechanism 45 comprises, e.g., an elevating motor 46 secured to the upper part of the rear surface of the wall plate 12, an elevating feed screw 47 extending downward from the elevating motor 46, and a nut 48 that meshes with the elevating feed screw 47, the nut being provided to the sample stand 16. When the elevating feed screw 47 is rotated forward and backward by the elevating motor 46, the nut 48 elevates or descends and the sample stand 16 elevates or descends.

A plurality of rollers 49 for sandwiching the wall plate 12 are preferably provided to the sample stand 16. Sandwiching the wall plate 12 with a plurality of rollers 49 allows the sample stand 16 to be elevated without shaking.

The elevating feed screw 47 is preferably a precision ball screw.

Figure 3:
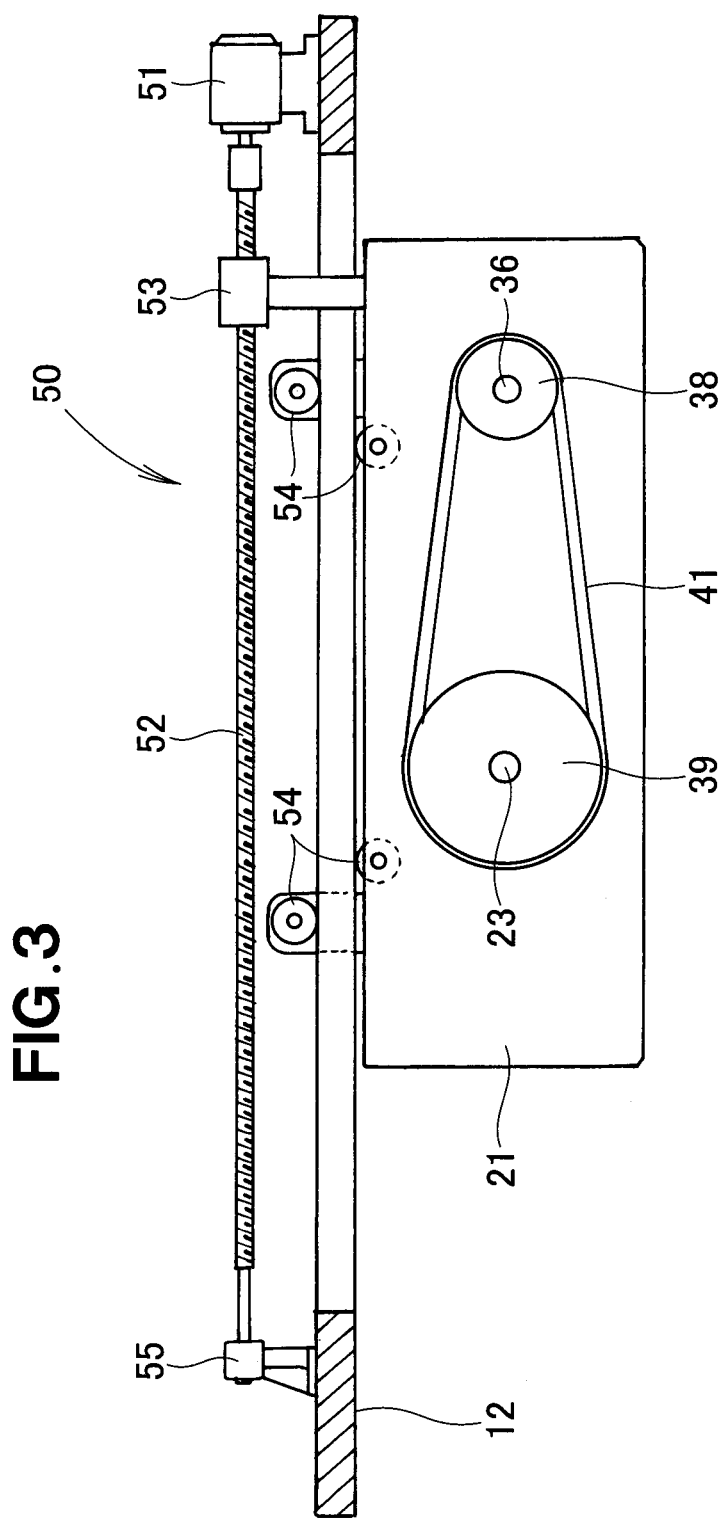
FIG. 3 is a cross-sectional view taken along line 3-3 of FIG. 1.

A slider movement mechanism 50 comprises, e.g., a stepper motor 51 secured to the back surface of the wall plate 12, a horizontal-movement feed screw 52 extending horizontally from the stepper motor 51, and a nut 53 that meshes with the horizontal-movement feed screw 52, the nut being provided to the slider 21, as shown in FIG. 3.

When the horizontal-movement feed screw 52 is caused to rotate by the stepper motor 51, the nut 53 moves and the slider 21 moves horizontally. The stepper motor 51, which is referred to as a control motor, is capable of controlling rotational speed and/or rotational angle (rotational distance).

The control motor is advantageously a stepper motor, but may be also be a servomotor.

A plurality of rollers 54 for sandwiching the wall plate 12 is preferably provided to the slider 21. Sandwiching the wall plate 12 with a plurality of rollers 54 allows the slider 21 to be moved without shaking.

The horizontal-movement feed screw 52 is advantageously a precision ball screw.

A screw support 55 for rotatably supporting the distal end of the horizontal-movement feed screw 52 is preferably provided to the wall plate 12. The horizontal-movement feed screw 52 is long and the distal end thereof can be prevented from run-out by the screw support 55.

Figure 4:
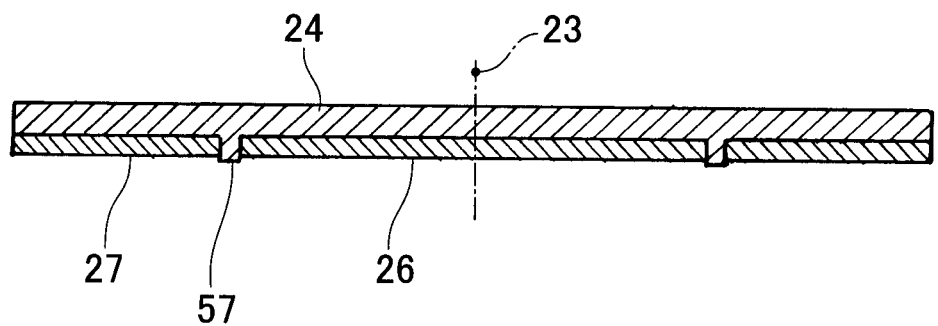
FIG. 4 is a cross-sectional view illustrating a turntable.

An annular partition wall 57 is integrated with the lower surface of the turntable 24, as shown in FIG. 4. A disc-shaped inner polishing cloth 26 is attached to the inner side of the partition wall 57 and to the lower surface of the turntable 24. Also, a donut-shaped outer polishing cloth 27 is attached to the outer side of the partition wall 57 and to the lower surface of the turntable 24. The inner polishing cloth 26 is a polishing cloth for finishing (mirror finishing), and the outer polishing cloth 27 is a polishing cloth for rough polishing. The mesh of the inner polishing cloth 26 is finer than that of the outer polishing cloth 27.

Figure 5:
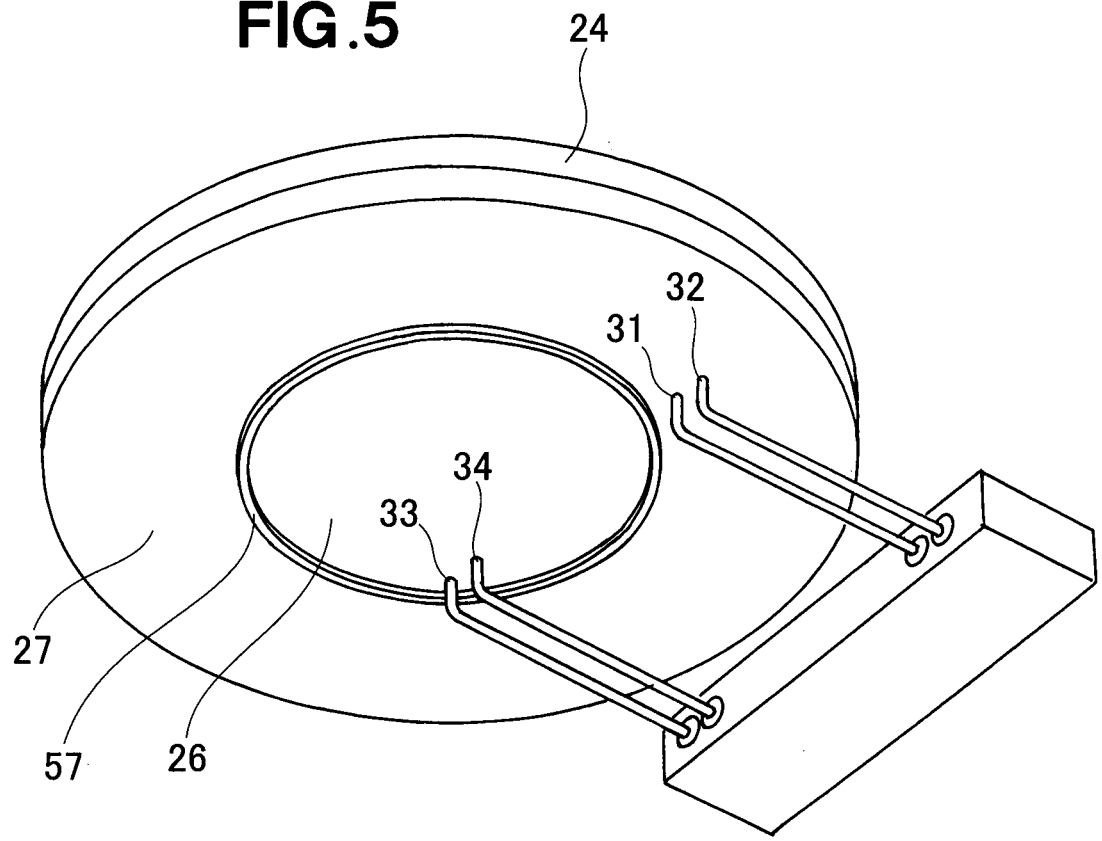
FIG. 5 is a view as seen in the direction of arrow 5 of FIG. 1.

The first polishing-liquid spray nozzle 31 and the first washing-liquid spray nozzle 32 are disposed below the outer polishing cloth 27, and the second polishing-liquid spray nozzle 33 and the second washing-liquid spray nozzle 34 are disposed below the inner polishing cloth 26, as shown in FIG. 5. The distal ends of the nozzles 31, 32 face the outer polishing cloth 27 and the distal ends of the nozzles 33, 34 face the inner polishing cloth 26.

Figure 6:
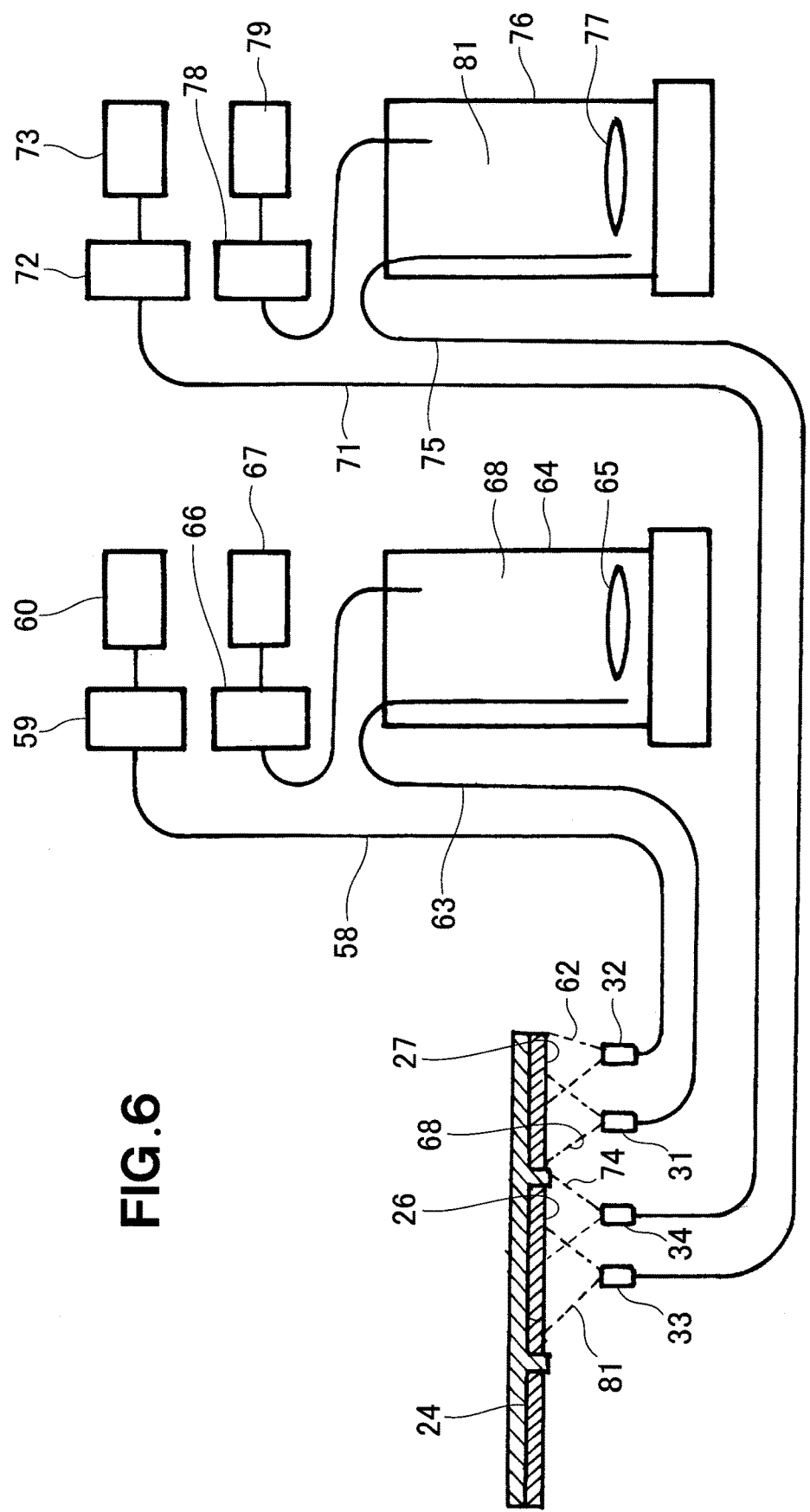
FIG. 6 is a schematic flow diagram of polishing liquid and washing liquid.

An automatic valve 59 and a washing-liquid supply source 61 are connected to the first washing-liquid spray nozzle 32 via a tube 58, as shown in FIG. 6. When the automatic valve 59 is opened, a first washing liquid 62 is sprayed from the first washing-liquid spray nozzle 32, and spraying stops when the automatic valve 59 is closed.

A first polishing-liquid container 64 is connected to the first polishing-liquid spray nozzle 31 via a tube 63. A magnetic stirrer 65 is accommodated in the first polishing-liquid container 64. An automatic valve 66 and a driving gas source 67 are furthermore connected to the first polishing-liquid container 64.

A first polishing liquid 68 containing micro-particulate polishing material is charged into the first polishing-liquid container 64. Stirring the liquid with the magnetic stirrer 65 prevents precipitation of the polishing material and contributes to dispersion.

When the automatic valve 66 is opened, the first polishing liquid 68 is compressed by high-pressure gas, which results in the first polishing liquid 68 being sprayed from the first polishing-liquid spray nozzle 31. Spraying stops when the automatic valve 66 is closed.

Similarly, an automatic valve 72 and a washing-liquid supply source 73 are connected to the second washing-liquid spray nozzle 34 via a tube 71. When the automatic valve 72 is opened, a second washing liquid 74 is sprayed from the second washing-liquid spray nozzle 34, and spraying stops when the automatic valve 72 is closed.

A second polishing-liquid container 76 is connected to the second polishing-liquid spray nozzle 33 via a tube 75. A magnetic stirrer 77 is accommodated in the second polishing-liquid container 76. An automatic valve 78 and a driving gas source 79 are connected to the second polishing-liquid container 76.

A second polishing liquid 81 containing micro-particulate polishing material finer than the micro-particles contained in the first polishing liquid 68 is charged into the second polishing-liquid container 76. Stirring the liquid with the magnetic stirrer 77 disperses the polishing material, eliminating any concern that polishing material will precipitate.

When the automatic valve 78 is opened, the second polishing liquid 81 is compressed by high-pressure gas, which results in the second polishing liquid 81 being sprayed from the second polishing-liquid spray nozzle 33. Spraying stops when the automatic valve 78 is closed.

Specifically, the first polishing liquid 68 is a polishing liquid for rough polishing and contains a polishing material having a relative large particle diameter. The second polishing liquid 81 is a polishing liquid for finishing and contains a polishing material having a relatively small diameter.

The operation of the observation and photography device configured as described above will be described with reference to FIGS. 7 to 9.

In FIG. 7(*a*), the turntable 24 is turned at a predetermined rotational speed (arrow (1)). The first polishing liquid 68 containing polishing material having a relatively large particle diameter is sprayed upward from the first polishing-liquid spray nozzle 31 toward the outer polishing cloth 27. Raising the sample stand 16 as shown by arrow (2) brings the upper surface of the sample 15 into contact with the outer polishing cloth 27 under a predetermined load. This contact is maintained for a predetermined length of time.

The first polishing liquid 68 is sprayed upward to wet the lower surface of the outer polishing cloth 27. The first polishing liquid 68 drops due to gravity from the outer polishing cloth 27. The polishing material (particles) provided to and crushed by polishing drops together with the first polishing liquid 68. Specifically, the degraded polishing liquid is separated from the polishing cloth.

Since the degraded polishing liquid is not retained on the polishing surface, there is no concern of unnecessary damage to the polishing surface, and the quality of the sample can kept high.

The first polishing liquid 68 strikes a portion of the outer polishing cloth 27, as shown in FIG. 7(*b*), which is a bottom surface view of the turntable 24. Since the outer polishing cloth 27 is rotating, the entire surface of the outer polishing cloth 27 is wetted by the first polishing liquid 68.

The wetted outer polishing cloth 27 makes contact with the sample 15 and the sample 15 is rough-polished. In this process, the first polishing liquid 68 is subjected to centrifugal force and is flung outward as shown by arrow (3). Consequently, there is no concern that the first polishing liquid 68 will infiltrate the inner polishing cloth 26.

When rough-polishing work has ended after a predetermined length of time at a predetermined rotational speed and under a predetermined load, the sample 15 is lowered (arrow (4)), as shown in FIG. 7(*c*). The slider 21 is subsequently moved as shown by arrow (5).

The sample 15 is moved to a suitable position for the inner polishing cloth 26 and then stopped, as shown in FIG. 8(*a*). The second polishing liquid 81 containing polishing material having a relatively small particle diameter is sprayed upward toward the inner polishing cloth 26 from the second polishing-liquid spray nozzle 33 toward the inner polishing cloth 26. Raising the sample stand 16 as shown by arrow (6) brings the upper surface of the sample 15 into contact with inner polishing cloth 26.

The upper surface of the sample 15 is finished using the inner polishing cloth 26 for a predetermined length of time at a predetermined rotational speed under a predetermined load, as shown in FIG. 8(*b*).

The second polishing liquid 81 strikes a portion of the inner polishing cloth 26, as shown in FIG. 8(*c*). Since the inner polishing cloth 26 is rotating, the entire surface of the inner polishing cloth 26 is wetted. The wetted inner polishing cloth 26 makes contact with the sample 15 and the sample 15 is finished. In this process, the second polishing liquid 81 is subjected to centrifugal force and gets flung radially outward as shown by arrow (7). However, the diameter of the polishing material particles is small, and rough polishing remains unaffected.

Figure 9:
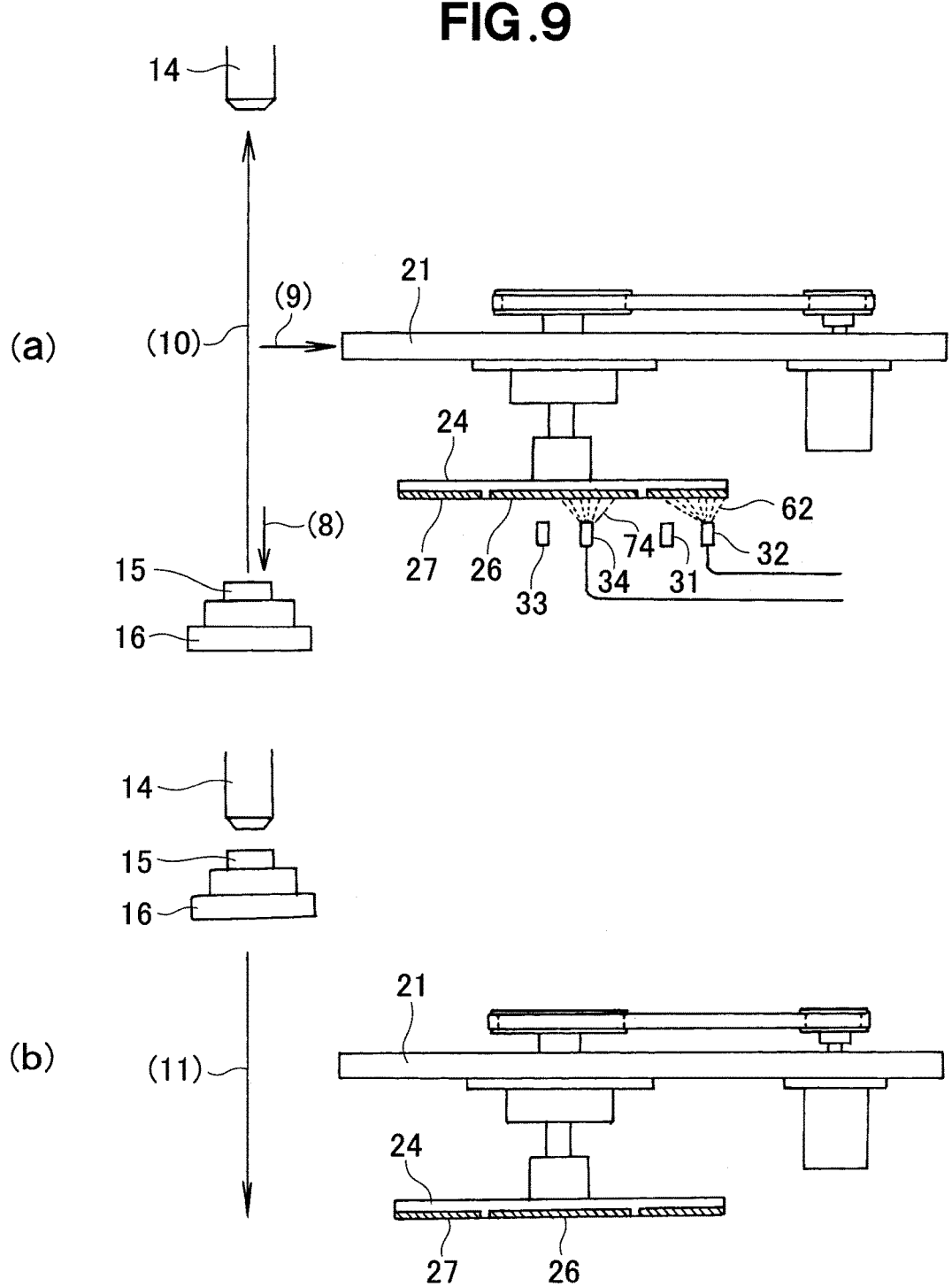
FIG. 9 is an operational view of the observation and photography device.

Since rough polishing and finishing have ended, the sample 15 is lowered (arrow (8)) and the slider 21 is subsequently returned to a standby position (arrow (9)), as shown in FIG. 9(*a*). The first washing liquid 62 is thereafter sprayed from the first washing-liquid spray nozzle 32 toward the lower surface of the outer polishing cloth 27 to clean the outer polishing cloth 27. The second washing liquid 74 is simultaneously sprayed from the second washing-liquid spray nozzle 34 toward the lower surface of the inner polishing cloth 26 to clean the inner polishing cloth 26.

The sample 15 is concurrently raised as shown by arrow (10).

The upper surface of the sample 15 is observed and/or photographed with the microscope 14, as shown in FIG. 9(*b*). The sample 15 is subsequently lowered to a standby position as shown by arrow (11).

The first polishing liquid 68 drops due to gravity from the outer polishing cloth 27, as shown in FIG. 7(*a*). The polishing material (particles) provided to and crushed by polishing drops together with the first polishing liquid 68.

Specifically, the degraded first polishing liquid 68 is separated from the outer polishing cloth 27.

Since the degraded first polishing liquid 68 is not retained on the polishing surface, there is no concern of unnecessary damage to the polishing surface, and the quality of the sample can kept high. Since the degraded first polishing liquid 68 is not retained on the polishing surface, there is no need for washing to be performed using large volumes of first washing liquid 62, and the required amount of first washing liquid 62 can be reduced.

The same applies to the second polishing liquid 81, as illustrated in FIGS. 8(a) and 8(b).

When only one type of polishing is required instead of two (rough polishing and finishing), a single disc-shaped polishing cloth can be attached to the turntable 24.

When three types of polishing (rough polishing, intermediate polishing, and finishing) are required, a single inner polishing cloth is fashioned to a small diameter, and the small-diameter inner polishing cloth 26 is surrounded by two strips (two rings) of outer polishing cloths in FIG. 4. Specifically, three concentric circular-strip polishing cloths can be provided to the turntable 24.

A configuration example of the polishing mechanism 20 is shown in FIG. 1, a configuration example of the sample stand-elevating mechanism 45 is shown in FIG. 2, and a configuration example of the slider movement mechanism 50 is shown in FIG. 3, but these configurations and layouts can be modified, as appropriate.

In the examples, the mesh of the inner polishing cloth is finer than that of the outer polishing cloth, but the outer polishing cloth and the inner polishing cloth can be given the same roughness and the particle diameter of the polishing material contained in the polishing liquid can be varied to implement rough polishing and finishing. Specifically, it is possible to implement rough polishing and finishing by selecting, as appropriate, from four combinations of varying or using the same roughness of the outer polishing cloth and the inner polishing cloth, and varying or using the same particle diameter of the polishing material contained in the polishing liquid to be sprayed from the first polishing-liquid spray nozzle and the polishing material contained in the polishing liquid to be sprayed from the second polishing-liquid spray nozzle.

Next, a different example will be described in which the inner polishing cloth is changed to a different cloth, and the inner polishing liquid is changed to a different liquid.

Making the inner polishing cloth to be an inner electrolyte-absorbing cloth and making the inner polishing liquid to be an electrolyte allows electrolytic polishing or electrolytic corrosion to be performed, or electrolytic corrosion and electrolytic polishing to be performed in combination.

Making the polishing cloth to be an electrolyte-absorbing cloth and making the polishing liquid spray nozzle to be an electrolyte spray nozzle will result in a spray of electrolyte upward from the electrolyte spray nozzle.

When the sample 15 has moved to a suitable position for the inner electrolyte-absorbing cloth 26, the slider 21 is stopped, as shown in FIG. 8(a). The turntable 24 is caused to rotate and an electrolyte 81 is sprayed upward toward the inner electrolyte-absorbing cloth 26 from the second electrolyte spray nozzle 33 toward the inner electrolyte-absorbing cloth 26. Raising the sample stand 16 as shown by arrow (6) brings the upper surface of the sample 15 into contact with the inner electrolyte-absorbing cloth 26.

At this point, an electric current is passed to the sample 15 and the inner electrolyte-absorbing cloth 26. A suitable insulating structure is used so that the sample 15 and inner electrolyte-absorbing cloth 26 do not become electrically short-circuited.

The turntable 24 may be used as an electrode. Also, an electrode may be attached to a portion in contact with the inner electrolyte-absorbing cloth 26. In the case of the latter, merely replacing the electrode will be sufficient; i.e., when the electrode has corroded, only the electrode need be replaced, which is advantageous in terms of cost.

The upper surface of the sample 15 is electrolytically polished or electrolytically corroded using the inner electrolyte-absorbing cloth 26 for a predetermined length of time at a predetermined rotational speed under a predetermined polishing load, as shown in FIG. 8(b).

The electrolyte 81 strikes a portion of the inner electrolyte-absorbing cloth 26, but since the inner electrolyte-absorbing cloth 26 is rotating, the entire surface of the inner electrolyte-absorbing cloth 26 is wetted, as shown in FIG. 8(c).

The wetted inner electrolyte-absorbing cloth 26 makes contact with the sample 15 and the sample 15 is electrolytically polished or electrolytically corroded. In this process, the electrolyte 81 is subjected to centrifugal force and flung outward as shown by arrow (7). However, the electrolyte 81 does not contain large particles and rough-polishing therefore remains unaffected.

Since electrolytic polishing or electrolytic corrosion has ended, the sample 15 is lowered (arrow (8)), and the slider 21 is subsequently returned to the standby position (arrow (9)), as shown in FIG. 9(a). Thereafter, the second washing liquid 74 is sprayed from the second washing-liquid spray nozzle 34 toward the lower surface of the inner electrolyte-absorbing cloth 26, and the inner electrolyte-absorbing cloth 26 is cleaned.

Since the degraded electrolyte is not retained on the polishing surface, there is no concern of superfluous foulants on the sample observation plane, and the quality of the sample can kept high. Since the degraded electrolyte is not retained in large quantities on the inner electrolyte-absorbing cloth 26, there is no need to wash the inner electrolyte-absorbing cloth 26 using large volumes of second washing liquid 74, and the required amount of second washing liquid 74 can be reduced.

Since polishing has ended, the amount of polishing is measured.

When electrolysis for forming irregular shapes on the surface of the sample is carried out, measurements are carried out prior to each cycle of electrolysis. The surface of the sample is preferably flat during the measurements.

When the sample 15 has moved to a position that corresponds to the laser measurement devices 83, 84, the slider is stopped, as shown in FIG. 10(a). Raising the sample stand 16 as shown by arrow (11) moves the sample 15 in the measureable range of the laser measurement devices 83, 84.

Polished locations are measured by one laser measurement device 83. Unpolished locations are measured by the other laser measurement device 84. The distance information obtained by the laser measurement device 83 and the distance information obtained by the laser measurement device 84 are inputted to the calculation unit (FIG. 1, reference numeral 86). The calculation unit determines the difference between the two distances, and uses [the result] as the amount of polishing.

When numerous positions are to be measured, the laser measurement devices 83, 84 are moved horizontally.

The distance information for the numerous positions obtained by the laser measurement devices 83, 84 is sent to the statistical processing unit (FIG. 1, reference numeral 85). The distance information for the numerous positions is statistically processed in the statistical processing unit to determine surface roughness. This statistical processing allows distances to be accurately measured even when the surface has irregular shapes.

Since electrolytic polishing or electrolytic corrosion, and measurement of the amount of polishing of the sample have ended, the slider 21 is subsequently returned to the standby position (arrow (9)), as shown in FIG. 9(a).

When observation of a sample is a structural observation, a Nital solution having nitric acid in a concentration of several percent or other corrosive liquid is often used as a method of selecting a structure and gray-scaling or coloring the structure to carry out observation. An advantageous configuration example of such a case is next described.

Figure 11:
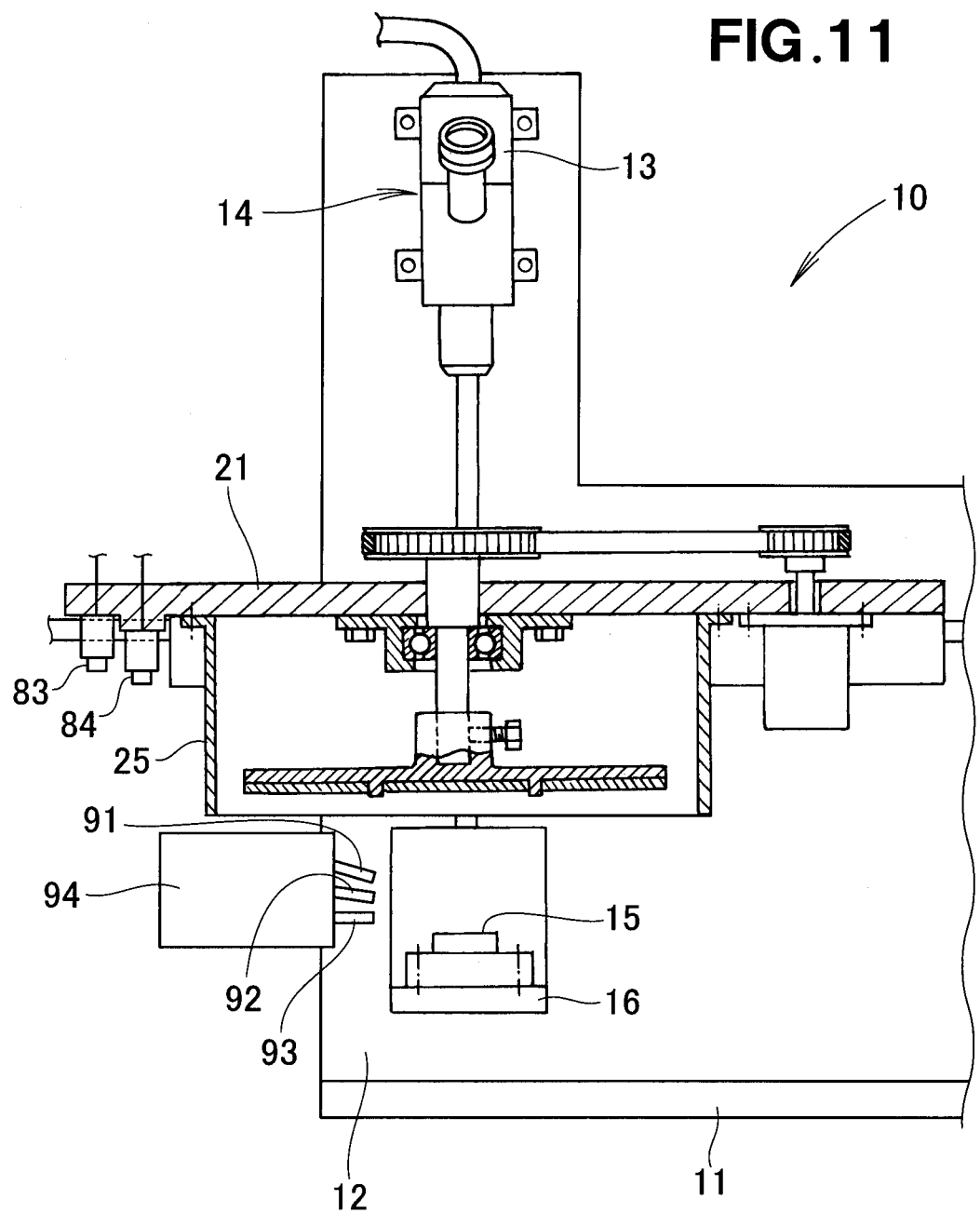
FIG. 11 is a view illustrating an arrangement example of a corrosive liquid nozzle, a washing nozzle, and a drying nozzle.
Figure 12:
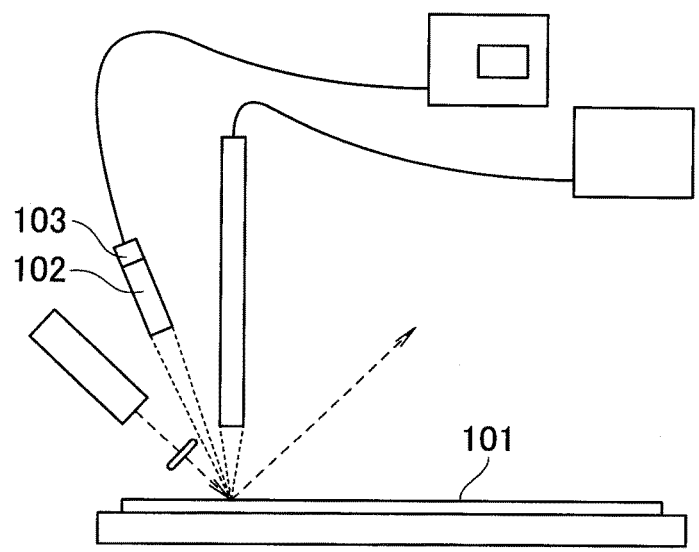
FIG. 12 is a view illustrating the basic principle of a conventional observation and photography device.
Figure 13:
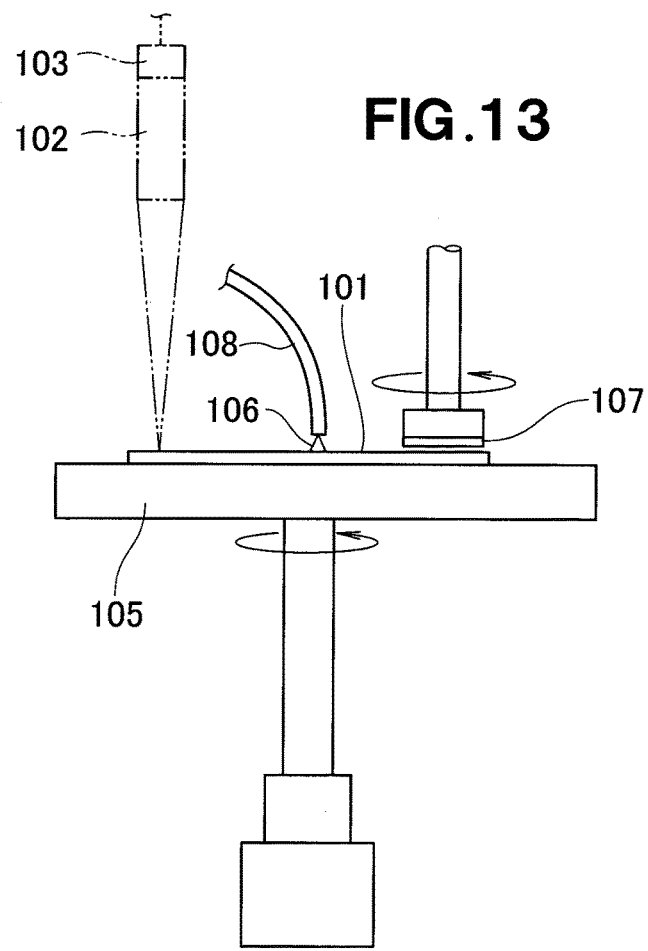
FIG. 13 is a view illustrating the basic principle of a separate conventional polishing mechanism.

A nozzle unit 94 is prepared, as shown in FIG. 11, the nozzle comprising a corrosion nozzle 91 for spraying corrosive liquid, a washing nozzle 92 for spraying washing liquid, and a drying nozzle 93 for spraying drying air. The cylindrical cover 25 and/or the slider 21 are interposed between the nozzle unit 94, and the microscope 14 and measurement devices 83, 84. Specifically, the nozzle unit 94 is disposed below or inside the cylindrical cover 25. The nozzle unit 94 may be attached to the wall plate 12 and is preferably attached to the cylindrical cover 25.

The spray area of the corrosion nozzle 91 and the washing nozzle 92 is surrounded by the cylindrical cover 25 and the lower surface of the slider 21, and there is accordingly no concern that droplets of corrosive liquid and/or droplets of washing liquid will land on the microscope 14 and/or the measurement devices 83, 84.

Water or warm water is sprayed from the washing nozzle 92. In the process of this spraying, it is recommended that the sample 15 be pivoted up and down to enhance the washing effect.

After corrosive liquid for etching has been applied to the sample, and it is recommended that the sample be washed using the washing nozzle 92 after several seconds to several minutes have elapsed. Chemical etching can be stopped by washing, and the amount of corrosion can be controlled with high precision. This direct washing can remove polishing liquid remaining on the sample.

Dry air, inert gas, and hot gas are sprayed from the drying nozzle 93. This spray makes it possible to remove remaining washing liquid and/or foulants while drying the surface of the sample 15.

In the process of blowing gas, it is recommended that the sample 15 be pivoted up and down to reduce drying time and eliminate drying marks.

There is no concern that droplets scattered by the drying nozzle 93 will be directed toward the microscope 14 and/or measurement devices 83, 84 due to the covering operation of the cylindrical cover 25.

Since electrolytic polishing or electrolytic corrosion, measurement of the amount of polishing of the sample, and washing and etching are completed, the slider 21 is returned to the standby position (arrow (9)), as shown in FIG. 9a.

Next, the sample 15 is raised (arrow (10)) and moved to the observation position of the microscope 14, and the polishing amount is estimated in this movement. Specifically, the upper surface of the sample 15 is lowered by the amount of polishing. In view of this fact, the sample stand 16 is raised by a movement amount increased by the measured amount of polishing or the value of the forecast setting for the amount of polishing. As a result, the surface of the sample 15 is constantly at the focal point of the microscope 14. The focus is adjusted by image recognition as may be required. This control is carried out in a single process by the control unit (FIG. 1, reference sign 87).

Although image blurring has been an issue in the past, clear images are constantly obtained according to the present invention as described above.

Furthermore, since information can be sent from the photography unit 13 to a monitor and the image can be observed on the monitor, as shown in FIG. 2, the eyepiece 43 can be omitted. Specifically, the microscope 14 in the present invention can be selected as desired from two modes: one provided with an eyepiece 43 and another that is not provided with an eyepiece 43.

As noted above, the microscope 14 is attached to the wall plate 12 via a manual or motor-driven XY stage 17 that moves in the horizontal direction. When a motor-driven stage is provided, a stepper motor, a servomotor, or another position control motor attached to the motor-driven stage is used. The microscope is moved by the position control motor, and mutually adjacent fields of view on the same polishing surface can be consecutively photographed. A first image is saved in a controlling PC prior to movement. The required image is photographed and saved so that the stage can be moved by controlling the motor movement distance and portions in which mutually adjacent images overlap can be obtained.

When the required images have finished being photographed, an operation is carried out to return the microscope XY stage to the field of view prior to movement by controlling the motor movement distance. At this point, the field of view may end up becoming misaligned depending on the mechanical precision or the like, but precision positioning relative to the first image, i.e., the image prior to movement, is carried out by image recognition. This control is also carried out in the control unit (FIG. 1, reference sign 87).

Mutually adjacent images of the same observation plane obtained by this action can be readily corrected for position displacement by the user to form a single image using commercially available image software separate from the present device.

INDUSTRIAL APPLICABILITY

The present invention is advantageous in an observation and photography device for observing and photographing the surface of a sample while repeatedly polishing the surface of the sample in equidistant intervals or an established amount.

REFERENCE SIGNS LIST

10: Observation and photography device
13: Photography unit
14: Microscope
15: Sample
17: Stage
20: Polishing mechanism
23: Rotation shaft
24: Turntable
26: Inner polishing cloth
27: Outer polishing cloth
31: Polishing-liquid spray nozzle (first polishing-liquid spray nozzle) doubling as a electrolyte spray nozzle
32: Washing-liquid spray nozzle (first washing-liquid spray nozzle)

33: Polishing-liquid spray nozzle (second polishing-liquid spray nozzle) doubling as an electrolyte spray nozzle or corrosive-liquid spray nozzle 34: Washing-liquid spray nozzle (second washing-liquid spray nozzle)

83, 84: Measurement device (non-contact-type laser measurement device)

85: Calculation unit

86: Statistical processing unit

87: Control unit

The invention claimed is:

1. An observation and photography device in which an electrolytic polishing mechanism is attached to a photography unit-equipped microscope capable of observing and photographing a surface of a sample, the electrolytic polishing mechanism repeatedly electrolytically polishing the surface of the sample in equidistant intervals or by an established amount in a vertical direction prior to observation, wherein the electrolytic polishing mechanism comprises: a turntable having a vertical rotation shaft; an electrolyte-absorbing cloth for absorbing electrolyte for electrolytically polishing an observation plane, the electrolyte-absorbing cloth being attached to a lower surface of the turntable; and an electrolyte-spraying nozzle for spraying the electrolyte upward to wet the electrolyte-absorbing cloth, the electrolyte-spraying nozzle being disposed below the electrolyte-absorbing cloth, wherein the turntable is disposed inside a cylindrical cover, the photography unit-equipped microscope is disposed outside the cylindrical cover, and a spray area of the polishing-liquid spray nozzle or the electrolyte spray nozzle is set inside the cylindrical cover.

2. The observation and photography device of claim 1, wherein a corrosive liquid is sprayed from the electrolyte-spraying nozzle.

3. The observation and photography device of claim 1, further comprising:
a gauge for gauging a distance to the surface of the sample or to the observation plane, and a calculation unit for calculating an amount of polishing from a difference between the distance prior to polishing and the distance after polishing, as gauged by the gauge.

4. The observation and photography device of claim 1, further comprising:
a gauge for gauging a distance to the surface of the sample or to the observation plane, and a statistical processing unit for measuring a plurality of locations on the surface or in the observation plane using the gauge, and statistically processing the plurality of resulting values to determine surface roughness.

5. The observation and photography device of claim 3, further comprising: a sample stand-elevating mechanism for moving the electrolytically or non-electrolytically polished sample to an observation position of the photography unit-equipped microscope, and a control unit for estimating the amount of polishing and controlling the sample stand-elevating mechanism so that the surface or the observation plane align with a focal point of the photography unit-equipped microscope.

6. The observation and photography device of claim 5, wherein the photography unit-equipped microscope is attached to a stage that moves horizontally, and the control unit saves an image prior to movement by the stage and has a control function for controlling the stage so that the photography unit-equipped microscope, which has been moved by the stage, returns to the original position on the basis of the image prior to movement.

* * * * *